United States Patent [19]

Ravichandran et al.

[11] Patent Number: 4,983,737
[45] Date of Patent: Jan. 8, 1991

[54] ETHYLENICALLY UNSATURATED COMPOUNDS CONTAINING 1-HYDROCARBYLOXY-2,2,6,6-TETRAMETHYLPIPERIDINE MOIETIES, AND POLYMERS, COPOLYMERS AND STABILIZED COMPOSITIONS

[75] Inventors: Ramanathan Ravichandran, Nanuet, N.Y.; Peter J. Schirmann, Fairfield, Conn.; Andrew Mar, Norwalk, Conn.

[73] Assignee: Ciba-Geigy Corporation, Ardsley, N.Y.

[21] Appl. No.: 479,912

[22] Filed: Feb. 14, 1990

Related U.S. Application Data

[63] Continuation-in-part of Ser. No. 326,705, Mar. 21, 1989.

[51] Int. Cl.$^5$ ............................................ C07D 211/00
[52] U.S. Cl. ...................................... 546/184; 546/186; 546/188; 546/190; 546/211; 546/216; 546/242; 546/244; 546/245
[58] Field of Search ............... 546/184, 186, 188, 190, 546/211, 216, 242, 244, 245

Primary Examiner—Joseph L. Schofer
Assistant Examiner—Alex H. Walker
Attorney, Agent, or Firm—Luther A. R. Hall

[57] ABSTRACT

Ethylenically unsaturated compounds containing 1-hydroxycarbyloxy-2,2,6,6-tetramethylpiperidine moieties represent reactable stabilizers which may be homopolymerized or copolymerized with other ethylenically saturated monomers to form non-migrating, light stabilizers which are very effective in stabilizing polyolefins and other polymer substrates against the deleterious effects of actinic light.

21 Claims, No Drawings

ETHYLENICALLY UNSATURATED COMPOUNDS CONTAINING 1-HYDROCARBYLOXY-2,2,6,6-TETRAMETHYL-PIPERIDINE MOIETIES, AND POLYMERS, COPOLYMERS AND STABILIZED COMPOSITIONS

This is a continuation-in-part of application Ser. No. 326,705, filed on Mar. 21, 1989.

The instant invention is to ethylenically unsaturated compounds containing 1-hydrocarbyloxy-2,2,6,6-tetramethylpiperidine moieties to polymers and copolymers made therefrom and to polymer compositions stabilized against the deleterious effects of actinic light by containing a stabilizing amount of said compounds.

BACKGROUND OF THE INVENTION

Monomeric copolymerizable light stabilizers which contain a hindered amine moiety are known in the art as the following list of typical patents and publications attest: U.S. Pat. Nos. 4,294,949; 4,210,612; 4,743,657; and F. Karrer, Makromol. Chem. 181, 595 (1980); K. W. Lee et al, J. Polym. Science, Poly Chem. Ed, 10, 3295 (1972); and T. Kuvosaki et al, J. Polym. Science, Poly. Chem. Ed, 12, 1407 (1974).

None of the above references discloses or suggests the instant compounds substituted on the 1-N atom by a hydrocarbyloxy group.

Non-polymerizable hindered amines substituted on the 1-N atom by hydrocarbyloxy groups are described in copending patent applications Ser. Nos. 259,956; 099,418; 259,950; 259,958; 259,945; 259,944; 259,952; 259,949; 259,955 and 259,946. However, the compounds described in these copending applications cannot be homopolymerized or copolymerized thus losing a key element of versatility available to the instant ethylenically unsaturated materials.

OBJECTS OF THE INVENTION

One object of the instant invention is to provide an ethylenically unsaturated, polymerizable monomer containing a hindered amine moiety substituted on the 1-N atom with a hydrocarbyloxy group.

Another object of the instant invention is to provide homopolymers of said monomers which have increased resistance to migration and to loss due to volatilization under end use conditions.

Still another object of this invention is to describe copolymers of said monomers with a wide variety of other ethylenically unsaturated monomers having no hindered amine moiety.

Yet another object of the invention is to provide polymer compositions which are stabilized against the deleterious effects of actinic light by having present a stabilizing amount of said monomer or of a polymer prepared from said monomer.

DETAILED DISCLOSURE

The instant invention is to an ethylenically unsaturated, polymerizable monomer containing a hindered amine moiety substituted on the 1-N atom with a hydrocarbyloxy group, said moiety having the formula E

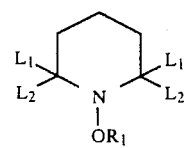

where $L_1$ and $L_2$ are independently alkyl of 1 to 4 carbon atoms, or $L_1$ and $L_2$ together are pentamethylene, and $R_1$ is hydrocarbyl, and said monomer is selected from the group consisting of formulas I–IX

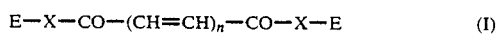

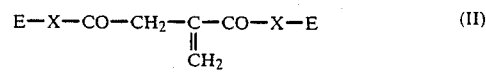

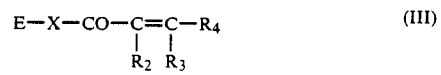

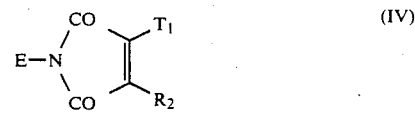

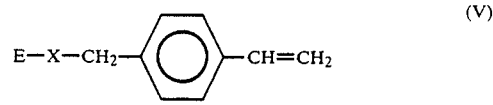

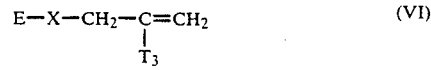

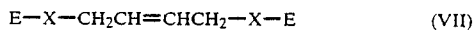

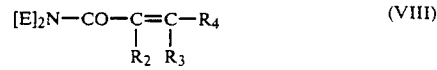

where $R_1$ is alkyl of 1 to 36 carbon atoms, alkenyl of 2 to 18 carbon atoms, alkynyl of 2 to 18 carbon atoms, aralkyl of 7 to 15 carbon atoms, cycloalkyl of 5 to 12 carbon atoms, cycloalkenyl of 5 to 12 carbon atoms, a radical of a saturated or unsaturated bicyclic or tricyclic hydrocarbon of 7 to 12 carbon atoms, or aryl of 6 to 10 carbon atoms or said aryl substituted by alkyl, X is a direct bond, -O(polyoxyalkyleneO)- of 2 to 12 carbon atoms, —O—, —NH— or —NG—, where G is alkyl of 1 to 8 carbon atoms, $X_1$ is a direct bond or —O—, n is 1 or 2, $T_1$, $T_2$ and $T_4$ are independently hydrogen, halogen, alkyl of 1 to 18 carbon atoms or aryl of 6 to 10 carbon atoms, $T_3$ is hydrogen or methyl, and $R_2$, $R_3$ and $R_4$ are independently hydrogen or alkyl of 1 to 12 carbon atoms, or $R_2$ is also cyano in formula III.

Preferably $L_1$ and $L_2$ are each methyl.

Preferably $R_1$ is alkyl of 1 to 18 carbon atoms, alkenyl of 2 to 3 carbon atoms, propargyl, benzyl or cyclohexyl.

G is preferably alkyl of 1 to 4 carbon atoms.

Preferably $T_1$ and $T_2$ are both hydrogen.

Preferably $T_3$ is hydrogen.

Preferably $R_2$, $R_3$ and $R_4$ are each hydrogen or $R_3$ and $R_4$ are hydrogen and $R_2$ is methyl.

When $R_1$ is alkyl, $R_1$ is, for example, methyl, ethyl, butyl, amyl, octyl, nonyl, dodecyl tetradecyl, octadecyl, eicosyl, tricosyl or tricontyl.

When $R_1$ is alkenyl, $R_1$ is for example, vinyl, allyl, octenyl or oleyl.

When $R_1$ is alkynyl, $R_1$ is, for example propargyl.

When $R_1$ is cycloalkyl, $R_1$ is for example, cyclopentyl, cyclohexyl, cyclooctyl or cyclododecyl.

Each of the monomers of formulas I to IX contains an ethylenically unsaturated group allowing the monomer to polymerize using free radical initiation, photoinitiation, group transfer polymerization, graft polymerization, or cationic or anionic polymerization to prepare either a homopolymer or a copolymer when more than one monomer of formula I to IX are copolymerized together.

Further, each of the monomers of formulas I to IX may be copolymerized with a separate vinyl monomer having no group of formula E present to yield a copolymer having as an integral part of the polymer backbone stabilizing units having pendant groups of formula E attached thereto.

Said polymer or copolymer comprises the polymerization product of (a) 1 to 100% by weight, based on the total polymer or copolymer, of at least one ethylenically unsaturated, polymerizable, monomer containing a hindered amine moiety substituted on the 1-N atom with a hydrocarbyloxy group, said moiety having the formula E

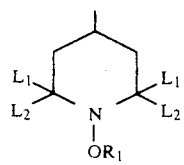

(E)

where $L_1$ and $L_2$ are independently alkyl of 1 to 4 carbon atoms or $L_1$ and $L_2$ together are pentamethylene, and $R_1$ is hydrocarbyl, and said monomer is selected from the group consisting of formulas I-IX

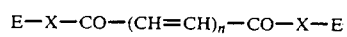

(I)

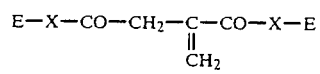

(II)

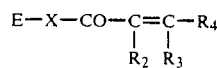

(III)

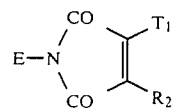

(IV)

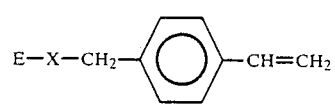

(V)

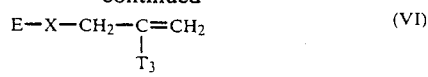

(VI)

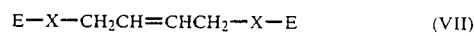

(VII)

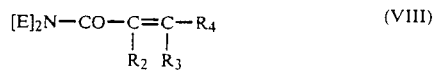

(VIII)

(IX)

where $R_1$ is alkyl of 1 to 36 carbon atoms, alkenyl of 2 to 18 carbon atoms, alkynyl of 2 to 18 carbon atoms, aralkyl of 7 to 15 carbon atoms, cycloalkyl of 5 to 12 carbon atoms, cycloalkenyl of 5 to 12 carbon atoms, a radical of a saturated or unsaturated bicyclic or tricyclic hydrocarbon of 7 to 12 carbon atoms, or aryl of 6 to 10 carbon atoms or said aryl substituted by alkyl, X is a direct bond, -O(polyoxyalkyleneO)- of 2 to 12 carbon atoms, —O—, —NH— or —NG—, where G is alkyl of 1 to 8 carbon atoms, $X_1$ is a direct bond or —O—, n is 1 or 2, $T_1$, $T_2$ and $T_4$ are independently hydrogen, halogen, alkyl of 1 to 18 carbon atoms or aryl of 6 to 10 carbon atoms, $T_3$ is hydrogen or methyl, and $R_2$, $R_3$ and $R_4$ are independently hydrogen or alkyl of 1 to 12 carbon atoms, or $R_2$ is also cyano in formula III.

(b) 99 to 0% by weight, based on the total polymer or copolymer, of at least one ethylenically unsaturated, polymerizable monomer having no group of formula E present and selected from the group consisting of the esters and amides of acrylic and methacrylic acid, the itaconates, the citraconates, styrene, the vinyl pyridines, divinylbenzene, acrylonitrile, methacrylonitrile, N-vinyl-2-pyrrolidone, N-vinylcarbazole, maleimides, vinyl sulfonate, vinyl phosphonates, alpha-olefins, isoprene, butadiene, vinyl esters, vinyl ethers and halogenated olefins.

Such copolymers, having even a small quantity of component (a) present, would have built in a high degree of light stabilizing units which cannot migrate, be lost by volatilization or otherwise leave the crucial site for protecting the copolymer from the deleterious effects of actinic light.

A still further aspect of the instant invention are stabilized compositions which comprise (A) an organic polymer subject to the deleterious effects of actinic light, and (B₁) a stabilizing amount of an ethylenically unsaturated, polymerizable monomer containing a hindered amine moiety substituted on the 1-N atom with a hydrocarbyloxy group, said moiety having the formula E

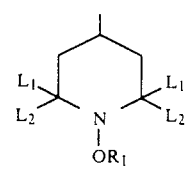

(E)

where $L_1$ and $L_2$ are independently alkyl of 1 to 4 carbon atoms, or $L_1$ and $L_2$ together are pentamethylene, and $R_1$ is hydrocarbyl, and said monomer is selected from the group consisting of formulas I-IX $$E-X-CO-(CH=CH)_n-CO-X-E \quad (I)$$

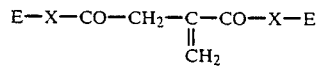
(II)

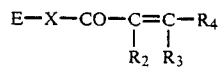
(III)

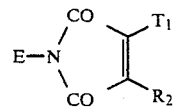
(IV)

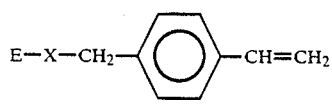
(V)

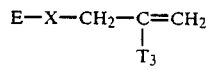
(VI)

$$E-X-CH_2CH=CHCH_2-X-E \quad (VII)$$

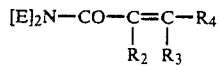
(VIII)

$$E-X_1-CT_1=CT_2T_4 \quad (IX)$$

where
- $R_1$ is alkyl of 1 to 36 carbon atoms, alkenyl of 2 to 18 carbon atoms, alkynyl of 2 to 18 carbon atoms, aralkyl of 7 to 15 carbon atoms, cycloalkyl of 5 to 12 carbon atoms, cycloalkenyl of 5 to 12 carbon atoms, a radical of a saturated or unsaturated bicyclic or tricyclic hydrocarbon of 7 to 12 carbon atoms, or aryl of 6 to 10 carbon atoms or said aryl substituted by alkyl,
- X is a direct bond, -O(polyoxyalkyleneO)- of 2 to 12 carbon atoms, —O—, —NH— or —NG—, where G is alkyl of 1 to 8 carbon atoms,
- $X_1$ is a direct bond or —O—,
- n is 1 or 2,
- $T_1$, $T_2$ and $T_4$ are independently hydrogen, halogen, alkyl of 1 to 18 carbon atoms or aryl of 6 to 10 carbon atoms,
- $T_3$ is hydrogen or methyl, and
- $R_2$, $R_3$ and $R_4$ are independently hydrogen or alkyl of 1 to 12 carbon atoms; or $R_2$ is also cyano in formula III; or (B2) a stabilizing amount of a polymer or copolymer which comprises the free radical polymerization product of (a) 1 to 100% by weight, based on the total polymer or copolymer, of at least one ethylenically unsaturated polymerizable monomer containing a hindered amine moiety substituted on the 1-N atom with a hydrocarbyloxy group, said moiety having the formula E

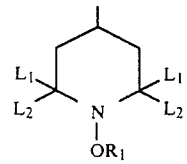
(E)

where $L_1$ and $L_2$ are independently alkyl of 1 to 4 carbon atoms, or $L_1$ and $L_2$ together are pentamethylene, and $R_1$ is hydrocarbyl, and said monomer is selected from the group consisting of formulas I-IX $$E-X-CO-(CH=CH)_n-CO-X-E \quad (I)$$

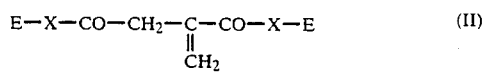
(II)

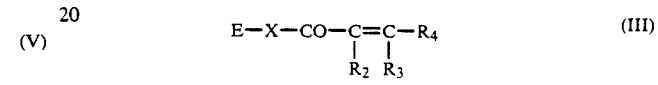
(III)

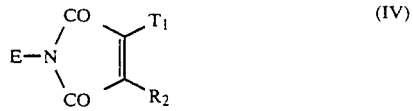
(IV)

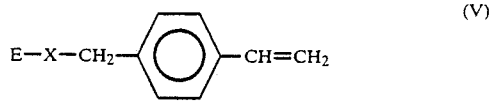
(V)

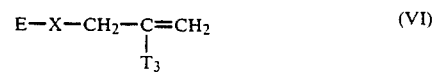
(VI)

$$E-X-CH_2CH=CHCH_2-X-E \quad (VII)$$

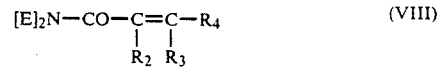
(VIII)

$$E-X_1-CT_1=CT_2T_4 \quad (IX)$$

where
- $R_1$ is alkyl of 1 to 36 carbon atoms, alkenyl of 2 to 18 carbon atoms, alkynyl of 2 to 18 carbon atoms, aralkyl of 7 to 15 carbon atoms, cycloalkyl of 5 to 12 carbon atoms, cycloalkenyl of 5 to 12 carbon atoms, a radical of a saturated or unsaturated bicyclic or tricyclic hydrocarbon of 7 to 12 carbon atoms, or aryl of 6 to 10 carbon atoms or said aryl substituted by alkyl,
- X is a direct bond, -O(polyoxyalkyleneO)- of 2 to 12 carbon atoms, —O—, —NH— or —NG—, where G is alkyl of 1 to 8 carbon atoms,
- $X_1$ is a direct bond or —O—,
- n is 1 or 2,
- $T_1$, $T_2$ and $T_4$ are independently hydrogen, halogen, alkyl of 1 to 18 carbon atoms or aryl of 6 to 10 carbon atoms,
- $T_3$ is hydrogen or methyl, and
- $R_2$, $R_3$ and $R_4$ are independently hydrogen or alkyl of 1 to 12 carbon atoms, or $R_2$ is also cyano in formula III; and (b) 99 to 0% by weight, based on the total polymer or copolymer, of at least one ethylenically unsaturated, polymerizable monomer having no group of formula E present and selected from the group consisting of the esters and amides of acrylic and methacrylic acid, the itaconates, the citraconates, styrene, the vinyl pyridines, divinylbenzene, acrylonitrile, methacrylonitrile, N-vinyl-2-pyrrolidone, N-vinylcarbazole, maleimides, vinyl sulfonate, vinyl phosphonates, alpha-olefins, isoprene, butadiene, vinyl esters, vinyl ethers and halogenated olefins.

The ethylenically unsaturated comonomers may also contain a UV-absorbing moiety such as a hydroxyphenyl substituted benzotriazole or s-triazine, a hydroxy substituted benzophenone, an oxanilide or alpha-cyanocinnamate. Examples of such ethylenically unsaturated UV-absorbers are described in a number of United States patents which are hereby incorporated into this application by references.

Acrylated benzotriazoles are described in U.S. Pat. Nos. 4,413,095; 4,716,234; 4,785,063 and 4,803,254. Acryloxyalkyl benzotriazoles are described in U.S. Pat. No. 4,260,768. Vinyl substituted benzotriazoles are described in U.S. Pat. No. 4,508,882. Ethylenically unsaturated benzotriazoles are described in U.S. Pat. No. 3,493,539. Acrylated benzophenones are described in U.S. Pat. No. 4,310,650.

There are several synthetic procedures which can be used to prepare the instant compounds.

These include:

(a) transesterification using a 4-hydroxy-2,2,6,6-tetramethylpiperidine and a lower alkyl ester of a unsaturated acid such as acrylic, fumaric, muconic or the like;

(b) esterification using a 4-hydroxy-2,2,6,6-tetramethylpiperidine and an acid chloride such as acryloyl or methacryloyl chloride;

(c) amidation using a 4-amino-2,2,6,6-tetramethylpiperidine and an acid chloride such as acryloyl or methacryloyl chloride;

(d) imidation using a 4-amino-2,2,6,6-tetramethylpiperidine and a cyclic anhydride such as maleic anhydride followed by cyclization of the intermediate maleamic acid;

(e) halide displacement using an unsaturated benzyl or allyl halide with the alkali metal alcoholate of 4-hydroxy-2,2,6,6-tetramethylpiperidine; and (f) catalytic oxidation of a preformed 4-acyloyloxy-2,2,6,6-tetramethylpiperidine with tert-butyl hydroperoxide or hydrogen peroxide in the presence of molybdenum trioxide catalyst and hydrocarbon solvent.

The intermediates needed to prepare the instant compounds are largely items of commerce or can be made by conventional methods known in the art.

Typical compounds of the instant invention include the following:

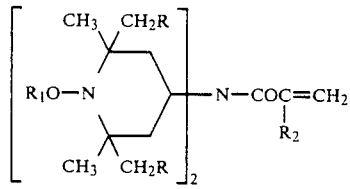

| R | $R_1$ | X | $R_2$ |
|---|---|---|---|
| H | allyl | —O— | H |
| H | allyl | —NH— | methyl |
| H | cyclohexyl | —O— | methyl |
| H | methyl | —O— | H |
| H | methyl | —N(n-butyl)— | H |
| methyl | octyl | —O— | H |
| H | methyl | —NH— | H |
| H | methyl | —NH— | methyl |
| H | cyclohexyl | —N(n-butyl)— | methyl |
| H | cyclohexyl | —NH— | methyl |
| H | octadecyl | —O— | methyl |
| H | benzyl | —O— | H |
| H | octyl | —O— | methyl |
| methyl | octyl | —O— | methyl |
| H | octyl | —NH— | H |
| H | octyl | —N(n-butyl)— | methyl |
| H | octyl | —NH | methyl |

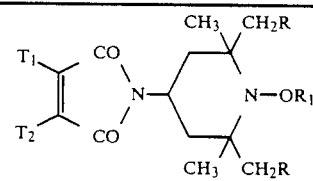

| R | $R_1$ | $R_2$ |
|---|---|---|
| H | cyclohexyl | methyl |
| H | methyl | H |
| H | methyl | methyl |
| H | cyclohexyl | H |
| H | octyl | H |
| H | octyl | methyl |
| methyl | octyl | methyl |
| H | allyl | H |
| H | allyl | methyl |
| H | octadecyl | H |
| H | octadecyl | methyl |

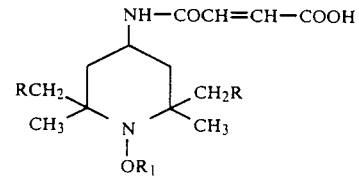

| R | $R_1$ | $T_1$ | $T_2$ |
|---|---|---|---|
| H | methyl | H | H |
| H | cyclohexyl | H | dodecyl |
| H | methyl | H | dodecyl |
| H | octyl | H | H |
| H | octyl | methyl | methyl |
| methyl | octyl | methyl | methyl |
| H | octyl | H | dodecyl |
| H | allyl | H | H |
| H | allyl | H | methyl |
| H | octadecyl | H | H |

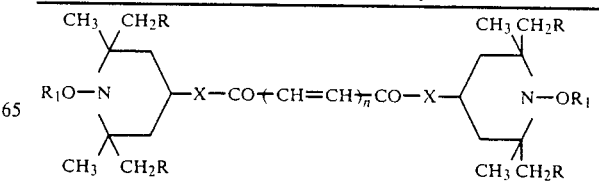

| R | $R_1$ |
|---|---|
| H | methyl |
| H | cyclohexyl |
| H | octyl |
| H | octadecyl |
| methyl | octyl |
| H | allyl |

-continued

| R | R₁ | N | X |
|---|---|---|---|
| H | cyclohexyl | 1 | —O— |
| H | cyclohexyl | 2 | —O— |
| H | methyl | 1 | —O— |
| methyl | octyl | 1 | —O— |
| methyl | octyl | 2 | —O— |
| H | octyl | 1 | —O— |
| H | octyl | 2 | —O— |
| H | allyl | 1 | —O— |
| H | octadecyl | 1 | —O— |
| H | cyclohexyl | 1 | —NH— |
| H | cyclohexyl | 1 | —N(n-butyl)— |
| H | methyl | 1 | —NH— |
| H | methyl | 1 | —N(n-butyl)— |
| H | octyl | 1 | —NH— |
| H | octyl | 1 | —N(n-butyl)— |
| H | allyl | 1 | —N(n-butyl)— |
| H | octadecyl | 1 | —N(n-butyl)— |

Although the instant application emphasizes the 2,2,6,6-tetraalkylpiperidine structure, it is to be noted that the invention also relates to compounds wherein the following tetraalkyl substituted piperazine or piperazinone moieties are substituted for the above-noted tetraalkylpiperidine moiety:

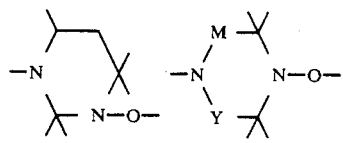

wherein M and Y are independently methylene or carbonyl, preferably M being methylene and Y being carbonyl. It is understood that the identified substituents applicable to such compounds are those which are appropriate for substitution on the ring nitrogen atoms.

Substrates in which the compounds of this invention are particularly useful are polyolefins such as polyethylene and polypropylene; polystyrene, including especially impact polystyrene; ABS resin; elastomers such as e.g. butadiene rubber, EPM, EPDM, SBR and nitrile rubber.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under (1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under (5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under (8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or silicone -acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene/-butadiene copolymers.

30. Polysiloxanes such as the soft, hydrophilic polysiloxanes described, for example, in U.S. Pat. No. 4,259,467; and the hard polyorganosiloxanes described, for example, in U.S. Pat. No. 4,355,147.

31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

32. Radiation curable compositions containing ethylenically unsaturated monomers or oligomers and a polyunsaturated aliphatic oligomer.

33. Epoxymelamine resins such as light-stable epoxy resins crosslinked by an epoxy functional coetherified high solids melamine resin such as LSE 4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain various conventional additives, such as the following.

1. Antioxidants 1.1. Alkylated monophenols, for example,
2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol 1.2. Alkylated hydroquinones, for example,
2,6-di-tert-butyl-4-methoxyphenol
2,5-di-tert-butyl-hydroquinone
2,5-di-tert-amyl-hydroquinone
2,6-diphenyl-4-octadecyloxyphenol 1.3. Hydroxylated thiodiphenyl ethers, for example
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)

1.4. Alkylidene-bisphenols, for example,
2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl] terephthalate.

1.5. Benzyl compounds, for example,
1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl) isocyanurate
1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt 1.6. Acylaminophenols, for example,
4-hydroxy-lauric acid anilide
4-hydroxy-stearic acid anilide
2,4-bis-octylmercapto-6-(3,5-tert-butyl-4-hydroxyanilino)s-triazine
octyl-N-(3,5-di-tert-butyl-4-hydroxyphenyl)-carbamate 1.7. Esters of β-(3,5-di-tert-butyl-4-hydroxyphenyl)-propionic acid with monohydric or polyhydric alcohols, for example,
methanol
octadecanol
1,6-hexanediol
neopentyl glycol
thiodiethylene glycol
diethylene glycol
triethylene glycol
pentaerythritol
tris-hydroxyethyl isocyanurate
di-hydroxyethyl oxalic acid
diamide 1.8. Esters of β-(5-tert-butyl-4-hydroxy-3-methylphenyl)propionic acid with monohydric or polyhydric alcohols, for example,
methanol
octadecanol
1,6-hexanediol
neopentyl glycol
thiodiethylene glycol
diethylene glycol
triethylene glycol
pentaerythritol
tris-hydroxyethyl isocyanurate
di-hydroxyethyl oxalic acid
diamide 1.9. Amides of β-(3,5-di-tert-butyl-4-hydroxyphenyl)-propionic acid for example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 2. UV absorbers and light stabilizers 2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxyocta-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl)-1,2,3,4-butanetetracarbonic acid, 1,1'(1,2-ethanediyl)-bis-(3,3,5,5-tetramethyl-piperazinone).

2.7. Oxalic acid diamides, for example, 4,4'-dioctyloxyoxanilide, 2,2'-di-octyloxy-5,5'-di-tert-butyloxanilide, 2,2'-di-dodecyloxy-5,5'-di-tert-butyl-oxanilide, 2-ethoxy-2'-ethyl-oxanilide, N,N'-bis (3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-as well as of o- and p-ethoxy-disubstituted oxanilides. 2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxyethoxy)phenyl]-6-phenyl-s-triazine; 2,4-bis[2-hydroxy-4-(2-hydroxyethoxy)phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearyl-sorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Polyamide stabilizers, for example copper salts in combination with iodides and/or phosphorus compounds and salts of divalent manganese.

8. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

9. Nucleating agents, for example, 4-tert-butyl-benzoic acid, adipic acid, diphenylacetic acid.

10. Fillers and reinforcing agents, for example, calcium carbonate, silicates, glass fibers, asbestos, talc, kaolin, mica, barium sulfate, metal oxides and hydroxides, carbon black, graphite.

11. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

Of particular interest is the utilization of the instant derivatives in a variety of coating systems including ambient cured and acid catalyzed coating systems. In particular, the physical integrity of the coatings is maintained to a higher degree with significant reduction in loss of gloss and yellowing. Key improvements include the substantial absence of the cure retardation encountered with N-alkyl hindered amine light stabilizers; the substantial absence of flocculation and dispersion destabilization seen when N-alkyl hindered amines are utilized in certain pigmented coating systems and the absence of adhesion loss between the coating and polycarbonate substrate. Accordingly, the present invention also relates to the use of the instant compounds, optionally together with further stabilizers, for stabilizing ambient cured coatings based on alkyd resins; thermoplastic acrylic resins; acrylic alkyds; acrylic alkyd or polyester resins optionally modified with silicon, isocyanates, isocyanurates, ketimines or oxazolidines; and epoxide resins crosslinked with carboxylic acids, anhydrides, polyamines or mercaptans; and acrylic and polyester resin systems modified with reactive groups in the backbone thereof and crosslinked with epoxides; against the degradative effects of light, moisture and oxygen.

Furthermore, in their industrial uses, enamels with high solids content based on crosslinkable acrylic, polyester, urethane or alkyd resins are cured with an additional acid catalyst. Light stabilizers containing a basic nitrogen group are generally less than satisfactory in this application. Formation of a salt between the acid catalyst and the light stabilizer leads to incompatibility or insolubility and precipitation of the salt and to a reduced level of cure and to reduced light protective action and poor resistance to moisture.

These acid catalyzed stoving lacquers are based on hot crosslinkable acrylic, polyester, polyurethane, polyamide or alkyd resins. The acrylic resin lacquers, which can be stabilized against light, moisture and oxygen in accordance with the invention, are the conventional acrylic resin stoving lacquers or thermosetting resins including acrylic/melamine systems which are described, for example, in H. Kittel's "Lehrbuch der Lacke und Beschichtungen", Vol. 1 Par 2, on pages 735 and 742 (Berlin 1972), "Lackkunstharze" (1977), by H. Wagner and H. F. Sarx, on pages 229-238, and in S. Paul's "Surface Coatings: Science and Technology" (1985).

The polyester lacquers, which can be stabilized against the action of light and moisture, are the conventional stoving lacquers described e.g. in H. Wagner and H. F. Sarx, op. cit., on pages 86-99.

The alkyd resin lacquers which can be stabilized against the action of light and moisture in accordance with the invention, are the conventional stoving lacquers which are used in particular for coating automobiles (automobile finishing lacquers), for example lacquers based on alkyd/melamine resins and alkyd/acrylic/melamine resins (see H. Wagner and H. F. Sarx, op. cit., pages 99-123). Other crosslinking agents include glycoluril resins, blocked isocyanates or epoxy resins.

The acid catalyzed stoving lacquers stabilized in accordance with the invention are suitable both for metal finish coatings and solid shade finishes, especially in the case of retouching finishes, as well as various coil coating applications. The lacquers stabilized in accordance with the invention are preferably applied in the conventional manner by two methods, either by the single-coat method or by the two-coat method. In the latter method, the pigment-containing base coat is applied first and then a covering coat of clear lacquer over it.

It is also to be noted that the instant substituted hindered amines are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines, and the like.

Correspondingly, the epoxide may be utilized as the crosslinking agent for various acrylic or polyester resin systems that have been modified by the presence of reactive groups on the backbone structure.

To attain maximum light stability in such coatings, the concurrent use of other conventional light stabilizers can be advantageous. Examples are the aforementioned UV absorbers of the benzophenone, benzotriazole, acrylic acid derivative, or oxanilide type, or aryl-s-triazines or metal-containing light stabilizers, for example organic nickel compounds. In two-coat systems, these additional light stabilizers can be added to the clear coat and/or the pigmented base coat.

If such combinations are employed, the sum of all light stabilizers is 0.2 to 20% by weight, preferably 0.5 to 5% by weight, based on the film-forming resin.

Examples of different classes of UV absorbers which may be used in the instant compositions in conjunction with the aforementioned piperidine compounds are referenced in a paper by H. J. Heller in European Polymer Journal Supplement, 1969, pp. 105–132. These classes include the phenyl salicylates, the o-hydroxybenzophenones, the hydroxyxanthones, the benzoxazoles, the benzimidazoles, the oxadiazoles, the triazoles, the pyrimidines, the chinazolines, the s-triazines, the hydroxyphenyl-benzotriazoles, the alpha-cyanoacrylates and the benzoates.

Types of UV absorbers of especial importance are:

(a) 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy-, and 3',5'-di-tert-amyl derivatives.

(b) 2-Hydroxy-benzophenones, for example, the 4-hydroxy-, 4-methoxy-, 4-octoxy-, 4-decyloxy-, 4-dodecyloxy-, 4-benzyloxy, 4,2',4'-trihydroxy- and 2'-hydroxy-4,4'-dimethoxy derivatives.

(c) Acrylates, for example, alpha-cyano-β,β-diphenylacrylic acid ethyl ester or isoctyl ester, alpha-carbomethoxy-cinnamic acid methyl ester, alpha-cyano-β-methyl-p-methoxy-cinnamic acid methyl ester or butyl ester, alpha-carbomethoxy-p-methoxy-cinnamic acid methyl ester, N-(β-carbomethoxy-β-cyanovinyl)-2-methyl-indoline.

(d) Nickel compounds, for example, nickel complexes of 2,2'-thiobis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketonoxime, nickel complexes of 1-phenyl-4-lauroyl-5-hydroxy-pyrazol, optionally with additional ligands.

(e) Oxalic acid diamides, for example, 4,4'-di-octyloxyoxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis-(3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and its mixtures of ortho- and paramethoxy- as well as of o- and p-ethoxy-disubstituted oxanilides.

(f) Hydroxyphenyl-s-triazines such as 2,6-bis(2,4-dimethylphenyl)-4-(2-hydroxy-4-octyloxyphenyl)-s-triazine or the corresponding 4-(2,4-dihydroxyphenyl) derivative.

Of particular value in the instant compositions are the benzotriazoles of high molecular weight and low volatility such as 2-[2-hydroxy-3,5-di(alpha,alpha-dimethylbenzyl)-phenyl]-2H-benzotriazole, 2-(2-hydroxy-3,5-di-tert-octylphenyl)-2H-benzotriazole, 2-(2-hydroxy-3-alpha,alpha-dimethylbenzyl-5-tert-octyl-phenyl)-2H-benzotriazole, 2-(2-hydroxy-3-tert-octyl-5-alpha,alpha-dimethylbenzylphenyl)-2H-benzotriazole, 2-(2-hydroxy-3,5-di-tert-amylphenyl)-2H-benzotriazole, 2-[2-hydroxy-3-tert-butyl-5-(2-(omega-hydroxy-octa-(ethyleneoxy)carbonyl)-ethylphenyl]-2H-benzotriazole, dodecylated 2-(2-hydroxy-5-methylphenyl)-2H-benzotriazole, 2-[2-hydroxy-3-tert-butyl-5-(2-octyloxycarbonyl)ethylphenyl]-2H-benzotriazole and the 5-chloro compounds corresponding to each of the above named benzotriazoles.

Most preferably the benzotriazoles useful in the instant compositions are 2-[2-hydroxy-3,5-di(alpha,alphadimethyl-benzyl)phenyl]-2H-benzotriazole, dodecylated 2-(2-hydroxy-5-methylphenyl)-2H-benzotriazole, 2-[2-hydroxy-3-tert-butyl-5-(2-(omega-hydroxy-octa-(ethyleneoxy) carbonyl)-ethylphenyl]-2H-benzotriazole, 2-[2-hydroxy-3-tert-butyl-5-(2-octyloxycarbonyl)ethylphenyl]-2H-benzotriazole and 5-chloro-2-[2-hydroxy-3-tert-butyl-5-(2-octyloxycarbonyl)ethylphenyl]-2H-benzotriazole.

It is also contemplated that the instant compounds will be particularly effective as stabilizers for polyolefin fibers, especially polypropylene fibers, when used in conjunction with other stabilizers selected from the group consisting of the phenolic antioxidants, hindered amine light stabilizers, organic phosphorus compounds, ultraviolet absorbers and mixtures thereof.

A further preferred embodiment of the instant invention is a stabilized composition containing components (a), (b) and (c) described above which additionally contains as component (d) a phosphite or phosphonite.

The amount of phosphite or phosphonite (d) which is used in the instant compositions is from 0.05 to 2% by weight, preferably from 0.1 to 1% by weight, based on the film forming resin. In two-coat systems, these stabilizers may be added to the clear coat and/or base coat.

Typical phosphite and phosphonites include triphenyl phosphite, diphenylalkyl phosphites, phenyldialkyl phosphites, tri-(nonylphenyl)phosphite, trilauryl phosphite trioctadecyl phosphite, di-stearyl-pentaerythritol diphosphite, tris-(2,4-di-tert.butylphenyl) phosphite, diisodecylpentaerythritol diphosphite, di-(2,4-di-tert.butylphenyl)pentaerythritol diphosphite, tristearylsorbitol triphosphite, tetrakis-(2,4-di-tert.butylphenyl)-4,4'-diphenylylenediphosphonite.

The acid catalyzed thermoset enamels must be stabilized in order to function acceptably in end-use applications. The stabilizers used are hindered amines, preferably those substituted on the N-atom by an inert blocking group in order to prevent precipitation of the basic amine stabilized with the acid catalyst with a concomitant retardation in cure, optionally in combination with UV absorbers, such as the benzotriazoles, benzophenones, substituted s-triazines, phenyl benzoates or oxanilides.

The stabilizers are needed to impart greater retention of durability to the cured enamels (as measured by 20° gloss, distinction of image, cracking or chalking); the stabilizers must not retard cure (normal bake for auto finishes at 121° C. and low bake repair at 82° C. (as measured by hardness, adhesion, solvent resistance and humidity resistance), the enamel should not yellow on curing and further color change on exposure to light should be minimized; the stabilizers should be soluble in the organic solvents normally used in coating applications such as methyl amyl ketone, xylene, n-hexyl acetate, alcohol and the like.

The instant hindered amine light stabilizers substituted on the N-atom by an O-substituted moiety fulfill each of these requirements and provide alone or in combination with a UV-absorber outstanding light stabilization protection to the cured acid catalyzed thermoset enamels.

A preferred embodiment of the instant invention pertains to stabilized compositions comprising (a) an acid catalyzed thermoset coating or enamel based on hot crosslinkable acrylic, polyester or alkyd resins, (b) a NO-$R_1$-substituted 2,2,6,6-tetralkylpiperidine compound, and (c) a UV absorber selected from the group consisting of the benzophenones, benzotriazoles, acrylic acid derivatives, organic nickel compounds, aryl-s-triazines and oxanilides.

Further ingredients which the enamels or coatings can contain are antioxidants, for example those of the sterically hindered phenol derivatives, phosphorus compounds, such as phosphites, phosphines or phosphonites, plasticizers, levelling assistants, hardening catalysts, thickeners, dispersants or adhesion promoters.

Still another preferred combination of the instant stabilizers is with a hydroxylamine in order to protect polypropylene fibers from gas fading.

The following examples are for illustrative purposes only and are not intended to limit the scope of the instant invention in any manner whatsoever.

EXAMPLE 1

Bis-(1-cyclohexyloxy-2,2,6,6-tetramethylpiperidin-4-yl) trans,trans-Muconate

A solution of 1.70 gram of dimethyl trans-trans-muconate, 5.62 grams of 1-cyclohexyloxy-2,2,6,6-tetramethylpiperidin-4-ol and 0.025 gram of lithium amide in 100 ml of toluene is heated under reflux with a Dean-Stark trap for 8 hours. The reaction mixture is then diluted with ethyl acetate, and then washed with water, brine and dried over anhydrous magnesium sulfate. Concentration under reduced pressure followed by chromatographic separation affords the title compound as a white solid.

EXAMPLE 2

1-Cyclohexyloxy-2,2,6,6-tetramethylpiperidin-4-yl Ester of Carboxy-terminated Polybutadiene (HYCAR 2000×162)

Oxalyl chloride (2.10 ml) is added to a solution of HYCAR 2000×162 (25.0 grams) in 75 ml of toluene. After stirring at room temperature for overnight, the reaction mixture is concentrated under reduced pressure to remove excess oxalyl chloride. The residue is dissolved in 50 ml of dry toluene and then treated with 3.06 grams of 1-cyclohexyloxy-2,2,6,6-tetramethylpiperidin-4-ol and 1.8 ml of triethylamine in 50 ml of toluene. After stirring overnight, the reaction mixture is filtered and concentrated under reduced pressure to afford the title compound as a light oil. Infrared and nmr analyses indicate complete reaction and incorporation of the hindered amine moiety into the polymer.

EXAMPLE 3

1-Cyclohexyloxy-2,2,6,6-tetramethyl-4-acryloyloxypiperidine

A solution of 1.6 ml of acryloyl chloride in 20 ml of methylene chloride is added to a stirred solution of 5.11 grams of 1-cyclohexyloxy-2,2,6,6-tetramethylpiperidin-4-ol and 3.10 ml of triethylamine in 20 ml of methylene chloride at 0° C. After stirring at room temperature for 2 hours, the solvent is removed under reduced pressure. The residue is then purified by liquid chromatography to afford the title compound as a white solid with a melting point of 49°–52° C.

Analysis: Calcd for $C_{18}H_{31}NO_3$: C, 69.9; H, 10.1; N, 4.5. Found: C, 70.0; H, 10.5; N, 4.5.

EXAMPLE 4

1-Cyclohexyloxy-2,2,6,6-tetramethyl-4-methacryloyloxypiperidine

The procedure of Example 3 is repeated using 5.11 grams of 1-cyclohexyloxy-2,2,6,6-tetramethylpiperidin-4-ol, 2.0 ml of methacryloyl chloride and 3.10 ml of triethylamine in methylene chloride. The above-named product is isolated as a colorless oil.

Analysis: Calcd for $C_{19}H_{33}NO_3$: C, 70.6; H, 10.3; N, 4.3. Found: C, 71.0; H, 10.6; N, 4.3.

EXAMPLE 5

1-Methoxy-2,2,6,6-tetramethyl-4-acryloyloxypiperidine

The procedure of Example 3 is repeated using 3.51 grams of 1-methoxy-2,2,6,6-tetramethylpiperidin-4-ol, 1.6 ml of acryloyl chloride and 3.10 ml of triethylamine in methylene chloride. The above-named product is isolated as a colorless liquid.

Analysis: Calcd for $C_{13}H_{23}NO_3$: C, 64.7; H, 9.6; N, 5.8. Found: C, 64.0; H, 9.8; N, 5.6.

1-Methoxy-4-methacryloyloxy-2,2,6,6-tetramethylpiperidine is made by substituting an equivalent amount of methacryloyl chloride in place of acryloyl chloride.

EXAMPLE 6

1-Cyclohexyloxy-2,2,6,6-tetramethyl-4-acrylamidopiperidine

The procedure of Example 3 is repeated using 3.0 grams of 4-amino-1-cyclohexyloxy-2,2,6,6-tetramethylpiperidine, 0.92 ml of acryloyl chloride and 1.8 ml of triethylamine in methylene chloride. The title compound is isolated as a white solid.

Analysis: Calcd for $C_{18}H_{32}N_2O_2$: C, 70.1; H, 10.5; N, 9.1. Found: C, 70.5; H, 10.8; N, 9.0.

EXAMPLE 7

N,N-Bis(1-cyclohexyloxy-2,2,6,6-tetramethylpiperidin-4-yl)acrylamide

The title compound is obtained when in the procedure of Example 6 an equivalent amount of N,N-bis(1-cyclohexyloxy-2,2,6,6-tetramethylpiperidin-4-yl)amine is substituted for 4-amino-1-cyclohexyloxy-2,2,6,6-tetramethylpiperidine.

EXAMPLE 8

1-Octyloxy-2,2,6,6-tetramethyl-4-acryloyloxypiperidine

The procedure of Example 3 is repeated using an equivalent amount of 1-octyloxy-2,2,6,6-tetramethylpiperidin-4-ol in place of 1-cyclohexyloxy-2,2,6,6-tetramethylpiperidin-4-ol to afford the title compound as a colorless liquid.

Analysis: Calcd for $C_{20}H_{37}NO_3$: C, 70.8; H, 11.0; N, 4.1. Found: C, 71.0; H, 10.8; N, 4.6.

EXAMPLE 9

4-Maleimido-1-cyclohexyloxy-2,2,6,6-tetramethylpiperidine

To a solution of 5.29 grams of 4-amino-1-cyclohexyloxy-2,2,6,6-tetramethylpiperidine in 50 ml of acetone is added dropwise over 10 minutes a solution of maleic anhydride (1.96 grams) in acetone. After heating under reflux for 30 minutes, the intermediate maleamic acid is obtained. A solution of the maleamic acid, sodium acetate (0.3 grams) and acetic anhdride (6.4 ml) is heated at 80° C. for two hours. The solution is then concentrated under reduced pressure and the residue purified by liquid chromatography to afford the title compound as a white solid with a melting point of 135°–139° C.

Analysis: Calcd for $C_{19}H_{30}N_2O_6$: C, 68.2; H, 9.0; N, 8.4. Found: C, 68.6; H. 9.3; N, 8.4.

EXAMPLE 10

1-Cyclohexyloxy-2,2,6,6-tetramethyl-4-vinylbenzyloxypiperidine

A solution of 1-cyclohexyloxy-2,2,6,6-tetramethylpiperidin-4-ol (5.11 grams in N,N-dimethylformamide) is added dropwise to a stirred suspension of sodium hydride (0.88 gram of a 60% dispersion). After stirring reaction mixture at room temperature for one hour and at 60° C. for 30 minutes, a solution of vinylbenzyl chloride (3.05 grams) in 5 ml of DMF is added. The reaction mixture is heated at 75° C. for seven hours. The reaction mixture is then concentrated under reduced pressure and the residue is partitioned between ethyl acetate and water. The organic layer is washed with water, dried over anhydrous magnesium sulfate and then evaporated to give a yellow oil. Preparative liquid chromatography affords the title compound as a light yellow oil.

Analysis: Calcd for $C_{24}H_{37}NO_2$: C, 77.6; H, 10.0; N, 3.8. Found: C, 77.4; H, 10.2; N, 3.7.

EXAMPLE 11

1-Octyloxy-2,2,6,6-tetramethyl-4-acryloyloxypiperidine

To a solution of 10.0 grams of 4-acryloyloxy-2,2,6,6-tetramethylpiperidin-1-oxyl in 150 ml of n-octane is added 0.6 gram of molybdenum trioxide. The resulting suspension is heated under reflux with a Dean-Stark trap in place. A 70% aqueous solution of tert-butyl hydroperoxide (17.0 grams) is added dropwise over a 30-minute period with removal of the azeotrope. After heating under reflux for eight hours, the colorless reaction mixture is cooled to room temperature and the suspended catalyst is removed by filtration. The filtrate is stirred with aqueous sodium bisulfite solution for one hour. The organic layer is washed with brine, dried over anhydrous magnesium sulfate and then evaporated. Liquid chromatography on the residue affords the title compound as a colorless liquid.

Analysis: Calcd for $C_{20}H_{37}NO_3$: C, 70.8; H, 11.0; N, 4.1. Found: C, 70.6; H, 11.1; N, 4.1.

EXAMPLE 12

4-Allyloxy-1-octyloxy-2,2,6,6-tetramethylpiperidine

Sodium hydride (2.65 grams, 110 mmol) is added to a solution of 30.0 grams (105 mmol) of 4-hydroxy-1-octyloxy-2,2,6,6-tetramethylpiperidine in 150 ml of tetrahydrofuran under nitrogen. The reaction mixture is heated at reflux for three hours, cooled to 35° C., and treated with 12.7 grams (110 mmol) of allyl bromide. The reaction mixture is heated at reflux for one hour, then partitioned between ethyl acetate (150 ml) and water (50 ml). The organic layer is washed with saturated sodium chloride solution (100 ml), dried over anhydrous magnesium sulfate, and concentrated under reduced pressure. The residue is dissolved in heptane (50 ml) and passed through a pad of silica gel (eluent 5:1 heptane:ethyl acetate). The crude product is purified by flash chromatography (silica gel; 9:1 heptane:ethyl acetate) to afford 23.9 grams (70% yield) of the title compound as a colorless oil.

Analysis: Calcd for $C_{20}H_{39}NO_2$: C, 73.8; H, 12.1; N, 4.3. Found: C, 74.0; H, 12.7; N, 4.7.

EXAMPLE 13

1-Octyloxy-4-methacryloyloxy-2,2,6,6-tetramethylpiperidine

The procedure of Example 3 is repeated using 1-octyloxy-4-hydroxy-2,2,6,6-tetramethylpiperidine, methacryloyl chloride and triethylamine in methylene chloride to afford the title compound as a colorless oil. Analyses by nmr, ir and ms give data consistent with the desired structure.

Analysis: Calcd for $C_{21}H_{39}NO_3$: C, 71.3; H, 11.1; N, 4.0. Found: C, 71.3; H, 11.2; N, 4.2.

EXAMPLE 14

Light Stabilization of Polypropylene

This example illustrates the light stabilizing effectiveness of instant stabilizers.

Polypropylene powder (Himont Profax 6501) stabilized with 0.2% by weight of n-octadecyl 3,5-di-tert-butyl-4-hydroxyhydrocinnamate is thoroughly blended with the indicated amount of additive. The blended materials are then milled on a two-roll mill at 182° C. for five minutes, after which time the stabilized polypropylene is sheeted from the mill and allowed to cool. The milled polypropylene is then cut into pieces and compression molded on a hydraulic press at 250° C. and 175 psi ($1.2 \times 10^6$ Pa) into 5 mil (0.127 mm) films. The sample is exposed in a fluorescent sunlight/black light chamber until failure. Failure is taken as the hours required to reach 0.5 carbonyl absorbance by infrared spectroscopy on the exposed films.

| Additive Compound of | Additive Concentration (% by weight) | FS/BL Test Results (hours to Failure) |
|---|---|---|
| Base Resin | — | 340 |
| Example 1 | 0.1 | 1290 |
| Example 2 | 0.1 | 460 |
| Example 3 | 0.1 | 1150 |
| Example 6 | 0.1 | 1010 |
| Example 9 | 0.1 | 1580 |
| Example 10 | 0.1 | 1090 |

EXAMPLE 15

A monomer composition comprising 23.5% butyl acrylate, 27% butyl methacrylate, 30% 2-hydroxyethyl acrylate, 15% styrene, 3% acrylic acid and 1.5% of the acrylate monomer prepared in Example 11 (all % values are by weight) and 0.4 phr of tert-amyl peroxy-O-(2-ethylhexyl) monoperoxy carbonate initiator is polymerized in refluxing xylene to form a stabilized acrylic polyol polymer having a molecular weight ($MW_n$) of 1300 and ($MW_w$) of 6000.

EXAMPLE 16

The stabilized acrylic polyol prepared in Example 15 is blended with sufficient unstabilized acrylic polyol, made by the same procedure of Example 15, but with the 1.5% by weight acrylate monomer of Example 11 being replaced with butyl acrylate, so that in the final acrylic-melamine formulation described below there is 1% of the hindered amine acrylate present based on total resin solids.

The acrylic-melamine formulation comprises (all values are in parts by weight) 70 parts of acrylic polyol mixture as described above, 18 parts of melamine (Cymel 303, American Cyanamid), 0.51 part of sulfonic acid catalyst (DDBSA Cycat, 70% 600, American Cyanamid), 0.6 part of flow aid (FC 431 50% solids fluorocarbon, 3M) and 8.8 parts of methyl amyl ketone.

Thermoset acrylic enamels are prepared using the formulations cited above.

Pieces of steel sheeting 4 in. × 12 in. (9.16 cm × 30.48 cm), coated with a polyester/epoxy primer, are then coated with a silver metallic base coat and finally with a clear finishing enamel. The basecoat is sprayed onto the coated sheet to a thickness of about 0.9 mil (0.023 mm) and air dried for three minutes.

The clear finishing enamel is then sprayed onto the sheet to a thickness of about 2 mils (0.05 mm). After air drying for ten minutes, the coated sheets are baked for thirty minutes at 250° C. (121° C. The Knoop hardness values of the baked coating is then determined.

| Knoop Hardness of High Solid Acid Cured Coatings | |
|---|---|
| Light Stabilizer Present (% by weight) | Knoop Hardness |
| Control | 9.3 |
| 1% Copolymer of Example 15 | 9.4 |
| 1% Copolymer of Example 15 plus 3% UV absorber* | 9.1 |
| 1% Copolymer of hindered amine having no N-OR$_1$ group** | 1.0 |

*2-(2-hydroxy-3,5-di-tert-amylphenyl)-2H-benzotriazole
**acrylic polyol made from 1,2,2,6,6-pentamethyl-4-acryloyloxypiperidine The effectiveness of cure is assessed from the Knoop hardness values. The higher numbers indicate greater hardness and better cure. The instant compounds having the N-hydrocarbyloxy group do not cause cure retardation as do compounds such as those having N-alkyl substitution.

After storage for 1 week in an air-conditioned room, these coated panels are then weathered in a QUV exposure apparatus according to ASTM G-53/77 using FS-40 bulbs.

| Acrylic Polymer (% by wt.) | 20 Degree Gloss Hours QUV Exposure (FS-40) | | | | | | | |
|---|---|---|---|---|---|---|---|---|
| | 0 | 925 | 1500 | 1808 | 2419 | 3168 | 3476 | 4088 |
| Control | 93 | 86 | 82 | 57* | | | | |
| 1% Copolymer of Example 15 | 94 | 91 | 85 | 83 | 76 | 53* | | |
| Control plus 3% UV Absorber** | 94 | 90 | 90 | 90 | 87 | 79 | 64 | 31 |
| 1% Copolymer of Example 15 plus 3% UV Absorber** | 94 | 91 | 90 | 92 | 86 | 85 | 84 | 82 |

*indicates cracking
**2-(2-hydroxy-3,5-di-tert-amylphenyl)-2H-benzotriazole

EXAMPLE 17

A two component acrylic urethane refinish coating based on a polyol composed of monomers such as 2-hydroxyethyl acrylate, butyl acrylate, butyl methacrylate, styrene, and acrylic acid and an aliphatic isocyanate crosslinking resin (Desmodur N-3390 from Mobay Corp) in a 1.05/1.00 ratio is formulated to include 1% by weight of hindered amine light stabilizer.

Commercially available 4"×12" (10.16 cm×30.48 cm) steel panels (Advanced Coatings Technology) are first primed with a commercial epoxy primer and then spray coated with a thermoplastic silver metallic basecoat to a thickness of about 0.8 mil (0.023 mm) and air dried for 5 minutes. The stabilized acrylic urethane clearcoat is then sprayed onto the basecoat to thickness of 1.7 mil (0.049 mm). After storage for 1 month in an air-conditioned room, the coated panels are weathered in a Xenon Arc Weatherometer. Gloss and Distinction-of-image are measured at 300 hour intervals.

| | 20 Degree Gloss Xenon Exposure (180 cam) | | | | | |
|---|---|---|---|---|---|---|
| | 0 Hours | | 853 Hours | | 2019 Hours | |
| Acrylic Polymer (% by wt.) | 20 Gloss | DOI | 20 Gloss | DOI | 20 Gloss | DOI |
| Control | 89 | 83 | 24 | 4 | 20 | 5 |
| 1% Copolymer of hindered amine having no N-OR group* | 89 | 76 | 78 | 46 | 39 | 9 |
| 1% Copolymer of Example 15 | 89 | 90 | 86 | 73 | 51 | 13 |
| 1% Copolymer of Example 15 plus 3% UV Absorber** | 89 | 90 | 91 | 85 | 82 | 73 |

*acrylic polyol made from 1,2,2,6,6-pentamethyl-4-acryloyloxypiperidine
**2-[2-hydroxy-3-tert-butyl-5-(2-(omega-hydroxy-octa-(ethyleneoxy)-carbonyl)-ethylphenyl]-2H-benzotriazole

EXAMPLE 18

A silver metallic acrylic alkyd enamel is stabilized with the indicated amounts of UV absorber and hindered amine derivative (by weight on total resin solids) and then spray applied to a thickness of 2.75 mils onto panels primed with an epoxy amine primer. After the coated panels aged at ambient temperature for one month, they are exposed in a Xenon Arc Weathermeter and 60 degree gloss is measured at 100 hour intervals.

| Formulation (% by wt.) | 60 Degree Gloss | | | |
|---|---|---|---|---|
| | Hours Xenon Exposure (180 cam) | | | |
| | 0 | 473 | 1024 | 1542 |
| Unstabilized | 90 | 30 | 13* | — |
| 2% UV Absorber plus 2% Compound of Example 9 | 90 | 63 | 24 | 18* |

*indicates cracking
**2-[2-hydroxy-3-tert-butyl-5-(2-omega-hydroxy-octa-(ethyleneoxy)-carbonyl)-ethylphenyl]-2H-benzotriazole

What is claimed is:

1. An ethylenically unsaturated, polymerizable monomer containing a hindered amine moiety substituted on the 1-N atom with a hydrocarbyloxy group, said moiety having the formula E

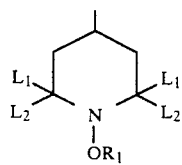

(E)

where $L_1$ and $L_2$ are independently alkyl of 1 to 4 carbon atoms, or $L_1$ and $L_2$ together are pentamethylene, and $R_1$ is hydrocarbyl, and said monomer is selected from the group consisting of formulas I-IX $$E-X-CO-(CH=CH)_n-CO-X-E \quad (I)$$

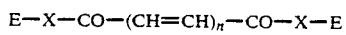  (II)

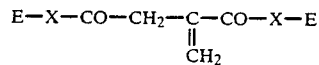  (III)

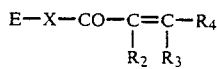  (IV)

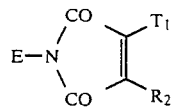  (V)

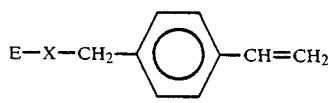  (VI)

$$E-X-CH_2CH=CHCH_2-X-E \quad (VII)$$

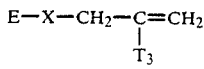  (VIII)

$$E-X_1-CT_1=CT_2T_4 \quad (IX)$$

where $R_1$ is alkyl of 1 to 36 carbon atoms, alkenyl of 2 to 18 carbon atoms, alkynyl of 2 to 18 carbon atoms, aralkyl of 7 to 15 carbon atoms, cycloalkyl of 5 to 12 carbon atoms, cycloalkenyl of 5 to 12 carbon atoms, a radical of a saturated or unsaturated bicyclic or tricyclic hydrocarbon of 7 to 12 carbon atoms, or aryl of 6 to 10 carbon atoms or said aryl substituted by alkyl, X is a direct bond, —O(polyoxyalkyleneO)— of 2 to 12 carbon atoms, —O—, —NH— or —NG—, where G is alkyl of 1 to 8 carbon atoms, $X_1$ is a direct bond or —O—, n is 1 or 2, $T_1$ $T_2$ and $T_4$ are independently hydrogen, halogen, alkyl of 1 to 18 carbon atoms or aryl of 6 to 10 carbon atoms, $T_3$ is hydrogen or methyl, and $R_2$, $R_3$ and $R_4$ are independently hydrogen or alkyl of 1 to 12 carbon atoms, or $R_2$ is also cyano in formula III.

2. A monomer according to claim 1 wherein $L_1$ and $L_2$ are each methyl.

3. A monomer according to claim 1 wherein $R_1$ is alkyl of 1 to 18 carbon atoms, alkenyl of 2 to 3 carbon atoms, propargyl, benzyl or cyclohexyl.

4. A monomer according to claim 1 wherein G is alkyl of 1 to 4 carbon atoms.

5. A monomer according to claim 1 wherein $T_1$ and $T_2$ are each hydrogen.

6. A monomer according to claim 1 wherein $T_3$ is hydrogen.

7. A monomer according to claim 1 wherein $R_2$, $T_3$ and $R_4$ are each hydrogen.

8. A monomer according to claim 1 wherein $R_2$ is methyl and $R_3$ and $R_4$ are both hydrogen.

9. The monomer according to claim 1 which is bis-(1-cyclohexyloxy-2,2,6,6-tetramethylpiperidin-4-yl) trans,-trans-muconate.

10. The monomer according to claim 1 which is 1-cyclohexyloxy-2,2,6,6-tetramethyl-4-acryloyloxypiperidine.

11. The monomer according to claim 1 which is 1-cyclohexyloxy-2,2,6,6-tetramethyl-4-methacryloyloxypiperidine.

12. The monomer according to claim 1 which is 1-methoxy-2,2,6,6-tetramethyl-4-acryloyloxypiperidine.

13. The monomer according to claim 1 which is 1-cyclohexyloxy-2,2,6,6-tetramethyl-4-acrylamidopiperidine.

14. The monomer according to claim 1 which is N,N-bis(1-cyclohexyloxy-2,2,6,6-tetramethylpiperidin-4-yl)acrylamide.

15. The monomer according to claim 1 which is 1-octyloxy-2,2,6,6-tetramethyl-4-acryloyloxypiperidine.

16. The monomer according to claim 1 which is 4-maleimido-1-cyclohexyloxy-2,2,6,6-tetramethylpiperidine.

17. The monomer according to claim 1 which is 1-cyclohexyloxy-2,2,6,6-tetramethyl-4-vinylbenzyloxypiperidine.

18. The monomer according to claim 1 which is 4-allyloxy-1-octyloxy-2,2,6,6-tetramethylpiperidine.

19. The monomer according to claim 1 which is 1-octyloxy-4-methacryloyloxy-2,2,6,6-tetramethylpiperidine.

20. The monomer according to claim 1 which is 1-methoxy-4-methacryloyloxy-2,2,6,6-tetramethylpiperidine.

* * * * *